United States Patent
Zou et al.

(10) Patent No.: US 11,733,259 B2
(45) Date of Patent: Aug. 22, 2023

(54) METHODS AND SYSTEM FOR CYCLE RECOGNITION IN REPEATED ACTIVITIES BY IDENTIFYING STABLE AND REPEATABLE FEATURES

(71) Applicant: Robert Bosch GmbH, Stuttgart (DE)

(72) Inventors: Linean Zou, San Jose, CA (US); Huan Song, San Jose, CA (US); Liu Ren, Saratoga, CA (US)

(73) Assignee: Robert Bosch GmbH, Stuttgart (DE)

(*) Notice: Subject to any disclaimer, the term of this patent is extended or adjusted under 35 U.S.C. 154(b) by 267 days.

(21) Appl. No.: 17/148,633

(22) Filed: Jan. 14, 2021

(65) Prior Publication Data

US 2022/0221482 A1  Jul. 14, 2022

(51) Int. Cl.
  *G01P 1/10* (2006.01)
  *G01P 1/12* (2006.01)
  *G01P 13/00* (2006.01)

(52) U.S. Cl.
  CPC ............. *G01P 1/106* (2013.01); *G01P 1/12* (2013.01); *G01P 13/00* (2013.01)

(58) Field of Classification Search
  CPC ............................ A61B 2503/10; G01P 1/106
  USPC ..................................................... 340/573.1
  See application file for complete search history.

(56) References Cited

U.S. PATENT DOCUMENTS

| 2016/0249832 | A1* | 9/2016 | Carter | A61B 5/0022 |
| | | | | 600/595 |
| 2020/0065608 | A1* | 2/2020 | Wolf | G06V 10/454 |
| 2020/0125839 | A1 | 4/2020 | Chen et al. | |
| 2020/0160044 | A1* | 5/2020 | Sur | G16H 50/50 |
| 2020/0209276 | A1 | 7/2020 | Zou et al. | |
| 2020/0335134 | A1* | 10/2020 | Gonzalez-Banos | G06F 16/7867 |
| 2020/0398110 | A1* | 12/2020 | Kosowsky | A63B 69/36 |

OTHER PUBLICATIONS

Berndt, D. J. et al., "Using Dynamic Time Warping to Find Patterns in Time Series," AAAI, AAAI Technical Report WS-94-03, 1994 (12 pages).

* cited by examiner

*Primary Examiner* — Fabricio R Murillo Garcia
(74) *Attorney, Agent, or Firm* — Maginot, Moore & Beck LLP

(57) ABSTRACT

A system and method for monitoring performance of a repeated activity is described. The system comprises a motion sensing system and a processing system. The motion sensing system includes sensors configured to measure or track motions corresponding to a repeated activity. The processing system is configured to process motion data received from the motion sensing system to recognize and measure cycle durations in the repeated activity. In contrast to the conventional systems and methods, which may work for repeated activities having a high level of standardization, the system advantageously enables recognition and monitoring of cycle durations for a repeated activity, even when significant abnormal motions are present in each cycle. Thus, the system can be utilized in a significantly broader set of applications, compared conventional systems and methods.

18 Claims, 5 Drawing Sheets

Feature candidates $F_i^j$ in cycle $C_i$
having feature length $W_k = 3$

METHODS AND SYSTEM FOR CYCLE RECOGNITION IN REPEATED ACTIVITIES BY IDENTIFYING STABLE AND REPEATABLE FEATURES

FIELD

The device and method disclosed in this document relates to human motion sensing and, more particularly, to analysis of human motion for a repeated activity.

BACKGROUND

Unless otherwise indicated herein, the materials described in this section are not admitted to be the prior art by inclusion in this section.

An important yet challenging problem in industry is the recognition of cycle durations in repeated physical human activities based on motion sensing data. For example, in an assembly line of a factory, workers perform repeated tasks to assemble a product. Accurate measurement and recognition of cycle durations for the repeated tasks facilitates the calculation of production volume and the recognition of manufacturing anomalies.

However, existing solutions for such monitoring are either labor intensive, requiring manual measurement of the cycles of the repeated tasks, or non-scalable, requiring a specialized device in the assembly line that usually only works for limited scenarios. Moreover, existing solutions often require a high level of standardization and consistency in the performance of each cycle of the repeated human activity, in terms of orientation and speed. Therefore, what is needed is a method and system for monitoring and recognizing cycle durations in repeated human activity that is cost effective and reliable, even when there is inconsistent performance of each cycle of the repeated human activity.

SUMMARY

A method for recognizing repetitions of a repeated activity is disclosed. The method comprises receiving, with a processor, first motion data corresponding to a first plurality of repetitions of a repeated activity, the first motion data including labels identifying time boundaries between each repetition in the first plurality of repetitions. The method further comprises identifying, with the processor, a salient segment of the first motion data corresponding to a motion of the repeated activity that occurs in all of the first plurality of repetitions. The method further comprises receiving, with the processor, second motion data corresponding to a second plurality of repetitions of the repeated activity from a motion sensing system. The method further comprises identifying, with the processor, time boundaries between each repetition in the second plurality of repetitions by detecting segments of the second motion data that are most similar to the salient segment of the first motion data.

A method for determining metadata of a repeated activity is disclosed. The method comprises receiving, with a processor, first motion data corresponding to a first plurality of repetitions of a repeated activity, the first motion data including labels identifying time boundaries between each repetition in the first plurality of repetitions. The method further comprises identifying, with the processor, a salient segment of the first motion data corresponding to a motion of the repeated activity that occurs in all of the first plurality of repetitions. The method further comprises storing, in a memory, metadata of the first motion data, the metadata including the salient segment of the first motion data.

A further method for recognizing repetitions of a repeated activity. The method comprises storing, in a memory, metadata of first motion data corresponding to a first plurality of repetitions of a repeated activity, the metadata including a salient segment of the first motion data corresponding to a motion of the repeated activity that occurs in all of the first plurality of repetitions. The method further comprises receiving, with the processor, second motion data corresponding to a second plurality of repetitions of the repeated activity from a motion sensing system. The method further comprises identifying, with the processor, time boundaries between each repetition in the second plurality of repetitions by detecting segments of the second motion data that are most similar to the salient segment of the first motion data. The method further comprises outputting, with an output device, the time boundaries between each repetition in the second plurality of repetitions.

BRIEF DESCRIPTION OF THE DRAWINGS

The foregoing aspects and other features of the methods and system are explained in the following description, taken in connection with the accompanying drawings.

DETAILED DESCRIPTION

Figure 1:
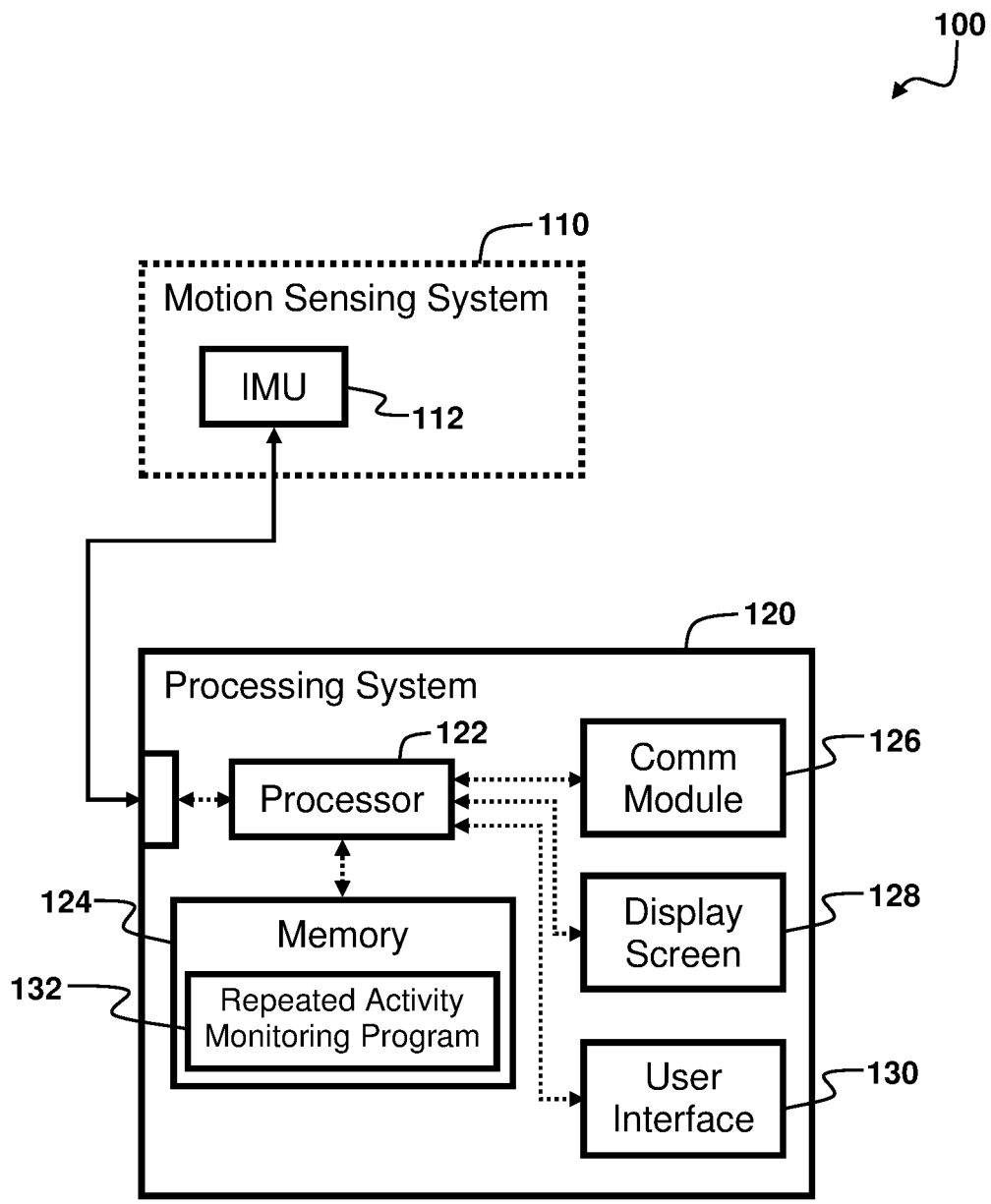
FIG. 1 shows a system for monitoring performance of a repeated activity.

For the purposes of promoting an understanding of the principles of the disclosure, reference will now be made to the embodiments illustrated in the drawings and described in the following written specification. It is understood that no limitation to the scope of the disclosure is thereby intended. It is further understood that the present disclosure includes any alterations and modifications to the illustrated embodiments and includes further applications of the principles of the disclosure as would normally occur to one skilled in the art which this disclosure pertains.

System Overview

FIG. 1 shows a system 100 for monitoring performance of a repeated activity. The system 100 at least comprises a motion sensing system 110 and a processing system 120. The motion sensing system 110 includes one or more sensors configured to measure or track motions corresponding to a repeated activity. The processing system 120 is configured to process motion data received from the motion sensing system 110 to recognize and measure cycle durations in the repeated activity. In contrast to the conventional systems and methods, which may work for repeated activities having a high level of standardization, the system 100 advantageously enables recognition and monitoring of cycle durations for a repeated activity, even when significant abnormal motions are present in each cycle. Particularly, each cycle may include abnormal motions that differ from other corresponding motions in other cycles, or even don't exist in other cycles, but these abnormalities do not affect the performance of the cycle recognition. Thus, the system 100 can be utilized in a significantly broader set of applications, compared conventional systems and methods.

In at least one embodiment, the repeated activity is a repeated human activity (also referred to herein as a "repeated task") comprising motions performed by a human. As an example, the repeated human activity may comprise the repeated motions involved in the assembly of a product by a worker in an assembly line of a factory. As another example, the repeated human activity may comprise the repeated motions involved in certain types of physical exercise by an athlete (e.g. repetitions, steps, etc.). As a further example, the repeated human activity may comprise the repeated motions involved in scanning products for checkout at a retail store by a cashier. Finally, it will be appreciated that, in principle, the tracked motions may correspond to a repeated activity that is performed by some robot, tool, or other object, which may be directed by a human or performed autonomously.

The motion sensing system 110 comprises at least one sensor configured to track the motions that comprise the repeated activity. In at least some embodiments, the motion sensing system 110 comprises at least one inertial measurement unit (IMU) 112. The IMU 112 includes one or more gyroscope sensors and one or more accelerometers configured to provide motion data in the form of acceleration and orientation measurements. In one embodiment, the IMU 112 comprises an integrated 6-axis inertial sensor that provides both triaxial acceleration measurements and triaxial gyroscopic/orientation measurements. In at least one embodiment, the IMU 112 is worn on the body of a human and may, for example, take the form of a wrist-worn watch or a hand-worn glove having the IMU 112 integrated therewith. In other embodiments, the IMU 112 may be integrated with an object that is carried by the human, such as a smartphone or a tool used in the repeated task.

In further embodiments, motion sensing system 110 may alternatively include other types of sensors than the IMU 112, such as an RGB-D camera, infra-red sensors, ultrasonic sensors, pressure sensors, or any other sensor configured to measure data characterizes a motion. Additionally, in some embodiments, the motion sensing system 110 may include multiple different types of sensors that provide multi-modal motion data that is processed in a multi-channel manner by the processing system 120, or which is fused using one or more sensor data-fusion techniques by the processing system 120 or other component of the system 100.

The processing system 120 is configured to process motion data captured by the motion sensing system 110 to recognize and measure cycle durations in the repeated activity. As used herein, a "cycle" refers to an individual repetition of a repeated activity. Advantageously, the processing system 120 is trained to measure cycle durations in a repeated activity based on only a limited set of motion data that has been manually labeled with cycle boundaries (i.e., at least start and end times for each individual cycle). Based on this limited set of labeled motion data, the processing system 120 determines the most salient features of the repeated activity and generates metadata of labeled motion data that is used to determine cycle durations in new unlabeled motion data.

In the illustrated exemplary embodiment, the processing system 120 comprises at least one processor 122, at least one memory 124, a communication module 126, a display screen 128, and a user interface 130. However, it will be appreciated that the components of the processing system 120 shown and described are merely exemplary and that the processing system 120 may comprise any alternative configuration. Particularly, the processing system 120 may comprise any computing device such as a desktop computer, a laptop, a smart phone, a tablet, or another electronic device. Thus, the processing system 120 may comprise any hardware components conventionally included in such computing devices.

The memory 124 is configured to store data and program instructions that, when executed by the at least one processor 122, enable the processing system 120 to perform various operations described herein. The memory 124 may be of any type of device capable of storing information accessible by the at least one processor 122, such as a memory card, ROM, RAM, hard drives, discs, flash memory, or any of various other computer-readable medium serving as data storage devices, as will be recognized by those of ordinary skill in the art. Additionally, it will be recognized by those of ordinary skill in the art that a "processor" includes any hardware system, hardware mechanism or hardware component that processes data, signals or other information. Thus, the at least one processor 122 may include a central processing unit, graphics processing units, multiple processing units, dedicated circuitry for achieving functionality, programmable logic, or other processing systems. Additionally, it will be appreciated that, although the processing system 120 is illustrated as single device, the processing system 120 may comprise several distinct processing systems 120 that work in concert to achieve the functionality described herein.

The communication module 126 may comprise one or more transceivers, modems, processors, memories, oscillators, antennas, or other hardware conventionally included in a communications module to enable communications with various other devices. In at least some embodiments, the communication module 126 includes a Wi-Fi module configured to enable communication with a Wi-Fi network and/or Wi-Fi router (not shown). In further embodiments, the communications module 126 may further include a Bluetooth® module, an Ethernet adapter and communications devices configured to communicate with wireless telephony networks.

The display screen 128 may comprise any of various known types of displays, such as LCD or OLED screens. In some embodiments, the display screen 128 may comprise a touch screen configured to receive touch inputs from a user. The user interface 130 may suitably include a variety of devices configured to enable local operation of the processing system 120 by a user, such as a mouse, trackpad, or other pointing device, a keyboard or other keypad, speakers, and a microphone, as will be recognized by those of ordinary skill in the art. Alternatively, in some embodiments, a user may operate the processing system 120 remotely from another computing device which is in communication therewith via the communication module 126 and has an analogous user interface.

The program instructions stored on the memory 124 include a repeated activity monitoring program 132. As discussed in further detail below, the processor 122 is configured to execute the repeated activity monitoring program 132 to process labeled motion data captured by the motion sensing system 110 to derive metadata describing the most salient features of a repeated activity. Additionally, the processor 122 is configured to execute the repeated activity monitoring program 132 to process unlabeled motion data captured by the motion sensing system 110 to recognize and measure cycle durations in the repeated activity.

Methods for Cycle Duration Recognition

Figure 2:
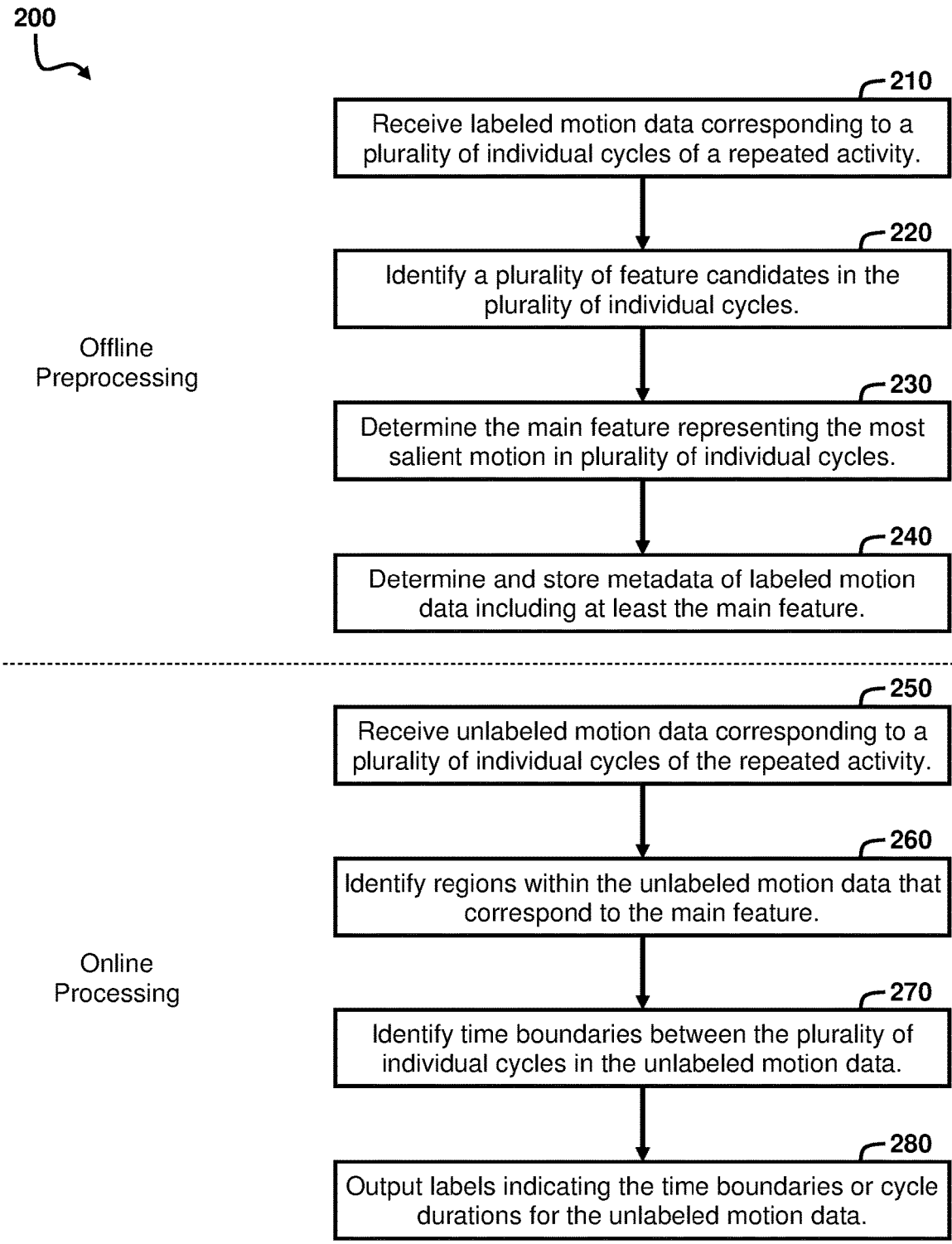
FIG. 2 shows a flow diagram for a method for recognizing cycle durations of a repeated activity.

FIG. 2 shows a flow diagram for a method 200 for recognizing cycle durations of a repeated activity. In the description of these method, statements that some task, calculation, or function is performed refers to a processor (e.g., the processor 122 of the processing system 120) executing programmed instructions stored in non-transitory computer readable storage media (e.g., the memory 124 of the processing system 120) operatively connected to the processor to manipulate data or to operate one or more components of the processing system 120 or the system 100 to perform the task or function. Additionally, the steps of the methods may be performed in any feasible chronological order, regardless of the order shown in the figures or the order in which the steps are described.

In summary, the method 200 has two major components: an offline preprocessing phase and an online processing phase. In the offline preprocessing phase, labeled motion data corresponding to a plurality of individual cycles of a repeated activity are provided as input. The labeled motion data includes labels that identify the time boundaries for each cycle of the repeated activity. A plurality of segments of the motion data are identified as feature candidates and each evaluated for their salience across all of the individual labeled cycles. For each labeled cycle, the feature candidate that is evaluated as most consistent across all of the individual labeled cycles is selected as the cycle feature, and most consistent one of the selected cycle features is selected as the main feature of the repeated activity. Finally, metadata describing the cycle features, the main feature, and other properties of the labeled cycles are determined and provided as an output.

Next, in the online processing phase, unlabeled motion data corresponding to a plurality of individual cycles of the repeated activity are provided as input. Cycle features are identified in the unlabeled motion data and cycle boundaries in unlabeled motion data are determined based on the identified cycle features. Based on the identified cycle boundaries in the unlabeled motion data, cycle durations are determined and provided as an output.

In greater detail and with continued reference to FIG. 2, the method 200 begins, in the offline preprocessing phase, with receiving labeled motion data corresponding to a plurality of individual cycles of a repeated activity (block 210). Particularly, the processor 122 receives a set of labeled motion data corresponding to a plurality of individual cycles of a repeated activity (e.g., 10-20 cycles). The processor 122 may read the labeled motion data from the memory 124 or from some other local storage medium, or the processor 122 may operate the communication module 126 to receive the labeled motion data from some other computing device or remote storage device. The labeled motion data includes labels that identify the time boundaries between each individual cycle of the repeated activity. In at least one embodiment, the labels are generated manually by a user. In at least some embodiments, the system 100 itself is configured to facilitate the capture and manual labeling of the labeled motion data using a graphical user interface or the like.

The method 200 continues, in the offline preprocessing phase, with identifying a plurality of feature candidates in the plurality of individual cycles (block 220). Particularly, the processor 122 identifies a plurality of feature candidate segments (also referred to herein as simply "feature candidates") of the labeled motion data. Each feature candidate is a continuous portion of the labeled motion data in a particular cycle of the plurality of individual cycles of the repeated activity. As will be described below, these feature candidates are evaluated for their salience and one or more are selected as being the most salient segment(s) and are used to identify cycles of the repeated activity in new unlabeled motion data.

In at least one embodiment, the processor 122 is configured to divide the labeled motion data into a plurality of frame segments (also referred to herein as simply "frames"). More particularly, the processor 122 divides each particular cycle of the labeled motion data into a respective plurality of frames. Each frame of each cycle of the labeled motion data corresponds to a discrete interval of time and, thus, comprises a continuous portion of the labeled motion data that was captured during the discrete interval of time. In at least one embodiment, each frame corresponds to a fixed duration of time (e.g., 2 seconds). Alternatively, in at least one embodiment, each frame corresponds to a duration of time that is a fixed percentage of the total duration of cycle (e.g., 10% of the cycle duration). In at least one embodiment, each frame is defined such that there is a predetermined amount of overlap with the previous frame and with the subsequent frame (e.g., 50% overlap).

Figure 3:
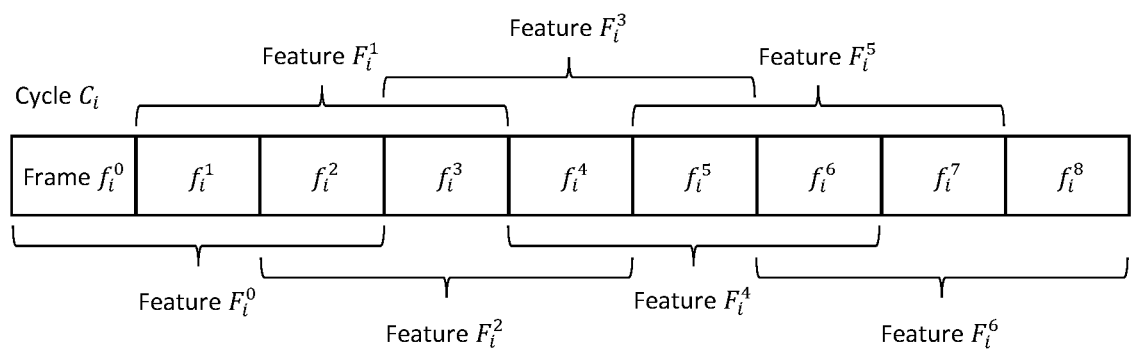
FIG. 3 shows an identification of feature candidates in an exemplary cycle of motion data of a repeated activity.

As noted above, the labeled motion data corresponds to a plurality of individual cycles of the repeated activity. Each individual cycle of the labeled motion data is denoted $C_i$, where $0 \leq i < N$ is the cycle index and N is the total number of cycles. Each cycle $C_i$ is divided into a plurality of frames $f_i^j$, where $0 \leq j < L_i$ is the frame index and $L_i$ is the total number of frames in the cycle $C_i$ or, in other words, $L_i$ is the length of cycle $C_i$. FIG. 3 shows an exemplary cycle of the labeled motion data. In the illustrated example, in which $L_i=9$, the cycle $C_i$ is divided into nine frames $f_i^0, \ldots, f_i^8$.

Next, the processor 122 is configured to group sets of consecutive frames together to form the plurality of feature candidate, denoted $F_i^j$. More particularly, for each individual cycle $C_i$ of the labeled motion data, the processor 122 groups sets of $W_k$ consecutive frames $f_i^j$ together to form a respective plurality of feature candidates $F_i^j$, where $W_k$ the total number of frames in each feature candidates $F_i^j$ or, in other words, $W_k$ is the length of each feature candidate $F_i^j$. Each feature candidate $F_i^j$ thus comprises the motion data of consecutive frames $f_i^j, \ldots, f_i^{j+W_k-1}$.

In at least one embodiment, for each individual cycle $C_i$, given a value for $W_k$, the processor 122 is configured to determine the plurality of feature candidates $F_i^j$ as including each possible combination of $W_k$ consecutive frames $f_i^j$ in the cycle individual cycle $C_i$. In other words, the processor 122 is configured to determine the plurality of feature candidates $F_i^j$ where $0 \leq j \leq M_i$ is the starting frame index of the feature candidates $F_i^j$ and $M_i = L_i - W_k$ is the starting frame index of that last in time feature candidate $F_i^j$. With continued reference to FIG. 3, an identification of feature candidates in the exemplary cycle $C_i$ of the labeled motion data is shown. In the illustrated example, in which $L_i=9$, $W_k=3$, and thus $M_i=6$, the cycle $C_i$ includes seven different feature candidates $F_i^0, \ldots, F_i^6$. The feature candidate $F_i^0$ includes the consecutive frames $f_i^0, f_i^1, f_i^2$, the feature candidate $F_i^1$ includes the consecutive frames $f_i^1, f_i^2, f_i^3$, and so on.

In one embodiment, at least initially, the processor 122 determines the plurality of feature candidates $F_i^j$ for each cycle $C_i$ only for a predetermined starting/minimum feature length $W_k$ (e.g., for $W_k=3$). However, in some embodiments, the processor 122 determines the plurality of feature candidates $F_i^j$ for each cycle $C_i$ for each of a range of feature lengths $W_k$ (e.g., for $W_k=3$, 4, 5).

Returning to FIG. 2, the method 200 continues, in the offline preprocessing phase, determining the main feature representing the most salient motion in plurality of individual cycles (block 230). Particularly, the processor 122 selects one or more salient feature segments from the plurality of feature candidate segments. As used herein, the term "salient feature" or "salient segment" refers to a segment of motion data that corresponds to a motion of a repeated activity that occurs relatively more consistently across cycles of the repeated activity compared to other motions in repeated activity and which is relatively more unique within individual cycles compared to other motions in repeated activity.

In at least some embodiments, the processor 122 selects a best or most salient feature in each individual cycle $C_i$ of the labeled motion data, which are referred to herein as cycle features. Particularly, the processor 122 determines the cycle feature for each individual cycle $C_i$, denoted $F_i^{best}$, as the feature candidate in the plurality of feature candidates $F_i^j$ that has a highest degree of similarity across corresponding regions of all of the labeled cycles $\{C_i\}_{i=0}^{N-1}$, and which can also be uniquely identified within each individual cycle $C_i$ (i.e., it doesn't occur multiple times within individual cycles). Thus, the processor 122 determines a set of N cycle features $\{F_i^{best}\}_{i=0}^{N-1}$, where each cycle feature $F_i^{best}$ is the most salient feature in the respective cycle $C_i$.

In at least some embodiments, after the set of cycle features $\{F_i^{best}\}_{i=0}^{N-1}$ is determined, the processor 122 selects one cycle feature from the set of cycle features $\{F_i^{best}\}_{i=0}^{N-1}$ as the main feature, denoted $F^{main}$, for the repeated activity. Particularly, the processor 122 determines which cycle feature from the set of cycle features $\{F_i^{best}\}_{i=0}^{N-1}$ has the highest degree of similarity across corresponding regions of all of the labeled cycles $\{C_i\}_{i=0}^{N-1}$.

As noted above, the cycle features $F_i^{best}$ and the main feature $F^{main}$ are selected from the feature candidates $F_i^j$ based on their degree of similarity across corresponding regions of all of the individual cycles $\{C_i\}_{i=0}^{N-1}$. Notably, since the different individual cycles $\{C_i\}_{i=0}^{N-1}$ may have different lengths and may include different motions, the corresponding regions of each other cycle $C_c$, where $c \neq i$, may have a different duration and timing compared to the feature candidate $F_i^j$. In at least one embodiment, for each feature candidate $F_i^j$ in each cycle $C_i$, the processor 122 determines the corresponding regions of each other cycle $C_c$, where $c \neq i$, using a dynamic time warping (DTW) algorithm. In this way, the corresponding regions describe the same or mostly similar motion, but may have different duration and timing.

Figure 4:
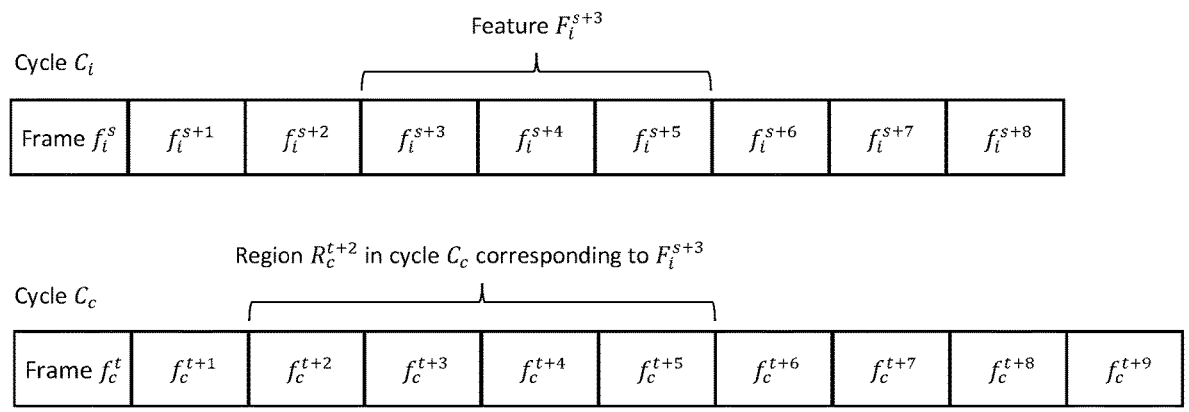
FIG. 4 shows a correspondence between regions of two exemplary cycles of motion data of a repeated activity.

FIG. 4 shows a correspondence between regions of exemplary cycles $C_i$ and $C_c$. In the illustrated example, the exemplary cycle $C_i$ has a length $L_i=9$ and has a feature candidate $F_i^{s+3}$ consisting of three frames $f_i^{s+3}, \ldots, f_i^{s+5}$ (i.e., $W_k=3$) corresponding to a motion that occurred roughly in the middle of the cycle $C_i$. In contrast, the exemplary cycle $C_c$ has a length $L_i=10$ and includes a region $R_c^{t+2}$ that corresponds to the same or mostly similar motion as the feature candidate $F_i^{s+3}$ of cycle $C_i$ and consists of four frames $f_c^{t+2}, \ldots, f_c^{t+5}$. Notably, the corresponding region $R_c^{t+2}$ of cycle $C_c$ has a different length and starting frame index than the feature candidate $F_i^{s+3}$ of cycle $C_i$. They correspond to the same motion, but were performed with slightly different speed and timing with their respective cycles.

In at least some embodiments, the processor 122 determines a respective evaluation score $S_i^j$ for each the plurality of feature candidates $F_i^j$ for each individual cycle $C_i$. The evaluation score $S_i^j$ indicates a degree of similarity between the feature candidate $F_i^j$ and the corresponding regions of each other cycle $C_c$, where $c \neq i$, in the plurality of individual cycles $\{C_i\}_{i=0}^{N-1}$. In at least one embodiment, the processor 122 calculates the evaluation score $S_i^j$ of a feature candidate $F_i^j$ as the average geometric distance/difference between the motion data of the feature candidate $F_i^j$ and the motion data of the corresponding regions of each other cycles $C_c$. Notably, as a result of the dynamic time warping, the evaluation score $S_i^j$ ignores temporal distance/difference between the motion data of the feature candidate $F_i^j$ and the motions of the corresponding regions of each other cycles $C_c$.

Once all of the evaluation scores $S_i^j$ for the plurality of feature candidates $F_i^j$ for each individual cycle $C_i$ are calculated, the processor 122 selects the feature candidate $F_i^j$ having the best score in each individual cycle $C_i$, as the respective cycle feature $F_i^{best}$ for each individual cycle $C_i$, thus deriving the set of cycle features $\{F_i^{best}\}_{i=0}^{N-1}$. It should be appreciated that, in the example in which the evaluation score $S_i^j$ an average distance/difference between corresponding regions across all cycles, the best score indicating the highest degree of similarity is the lowest average distance/difference. Finally, the processor 122 selects the cycle feature $F_i^{best}$ in the set of cycle features $\{F_i^{best}\}_{i=0}^{N-1}$ having the best score as the main feature $F^{main}$ for the repeated activity.

As noted above, the cycle features $F_i^{best}$ and the main feature $F^{main}$ for the repeated activity should be uniquely identifiable within each individual cycle $C_i$. In some embodiments, the processor 122 evaluates the uniqueness of the cycle features $F_i^{best}$ (or the main feature $F^{main}$) by determining a uniqueness score as an average geometric distance/difference between the motion data of the cycle feature $F_i^{best}$ and the motions data of each other feature candidate $F_i^j$ in the same cycle $C_i$. In this case a higher average geometric distance/difference indicates a more unique feature. In some embodiments, the feature length $W_k$ is be gradually increased so that the cycle features $F_i^{best}$ and the main feature $F^{main}$ are significantly different from other feature candidates within their respective cycles. In one embodiment, the processor 122 increases the feature length $W_k$ until a threshold uniqueness score is achieved.

The method 200 continues, in the offline preprocessing phase, with determining and storing metadata of labeled motion data including at least the main feature (block 240). Particularly, the processor 122 writes to the memory 124 metadata of the labeled motion data, which at least includes the main feature $F^{main}$ for the repeated activity. In some embodiments, the stored metadata of the labeled motion data further includes the set of cycle features $\{F_i^{best}\}_{i=0}^{N-1}$. As detailed below, the stored metadata will be used to identify cycles of the repeated activity in new unlabeled motion data.

In some embodiments, the stored metadata of the labeled motion data further includes a previously determined evaluation score $S^{main}$ for the main feature $F^{main}$. In some embodiments, the stored metadata of the labeled motion data further includes a previously determined set of evaluation scores $\{S_i^{best}\}_{i=0}^{N-1}$ for the set of cycle features $\{F_i^{best}\}_{i=0}^{N-1}$.

Figure 5:
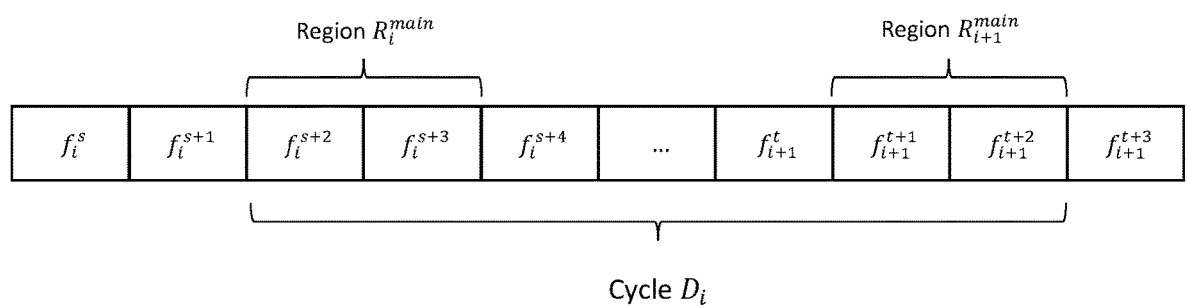
FIG. 5 shows an exemplary re-aligned cycle of a repeated activity.

In some embodiments, the stored metadata of the labeled motion data further includes the plurality of individual cycles $\{C_i\}_{i=0}^{N-1}$ (i.e., the original labeled motion data itself). In one embodiment, the stored metadata of the labeled motion data further includes a plurality of re-aligned cycles $D_i$ that start and end with regions corresponding to the main feature $F^{main}$ in the plurality of individual cycles $\{C_i\}_{i=0}^{N-1}$. FIG. 5 shows an exemplary re-aligned cycle $D_i$. In the illustrated example, the re-aligned cycle $D_i$ starts from a region $R_i^{main}$ in the cycle $C_i$ that corresponds to the main feature $F^{main}$ and ends with the region $R_{i+1}^{main}$ in cycle $C_{i+1}$ that corresponds to the main feature $F^{main}$. Thus, the processor 122 determines a set of re-aligned cycles $\{D_i\}_{i=0}^{N-2}$. In some embodiments, the re-aligned cycle $D_i$ ends at the end of the region $R_{i+1}^{main}$, such that the re-aligned cycle $D_i$ includes the region $R_{i+1}^{main}$ as shown in FIG. 5. However, in other embodiments, the re-aligned cycle $D_i$ ends at the start of the entirety of the region $R_{i+1}^{main}$, such that the re-aligned cycle $D_i$ does not include the region $R_{i+1}^{main}$. It should be appreciated that a re-aligned cycle cannot be determined for the final cycle $C_{N-1}$ because there is no subsequent cycle and, thus, there are one fewer re-aligned cycles $D_i$ than input cycles $C_i$. In some embodiments, the processor 122 similarly determines, and stores in the metadata, a respective set of re-aligned cycles $D_i$ for each of the N cycle features $F_i^{best}$.

Returning to FIG. 2, the method 200 continues, in the online processing phase, with receiving unlabeled motion data corresponding to a plurality of individual cycles of the repeated activity (block 250). Particularly, the processor 122 receives unlabeled motion data corresponding to a plurality of individual cycles of a repeated activity. More particularly, the processor 122 receives a stream of unlabeled motion data from the sensors (e.g., the IMU 112) of motion sensing system 110 and writes the stream of unlabeled motion data to the memory 124, for example in a buffer that is implemented on the memory 124. Unlike the labeled motion data utilized in the offline preprocessing phase, the unlabeled motion data received in the online processing phase does not includes labels that identify the time boundaries between each individual cycle of the repeated activity. Instead, the system 100 will identify these boundaries based on the stored metadata of the labeled motion data.

The processor 122 is configured to accumulate unlabeled motion data in the buffer, without further processing, until a threshold amount of unlabeled motion data is accumulated. In at least one embodiment, the processor 122 is configured to divide the unlabeled motion data into a plurality of frame, preferably having the same length as the frames of the unlabeled motion data (e.g., 2 seconds). In at least one embodiment, each frame is defined such that there is a predetermined amount of overlap with the previous frame and with the subsequent frame (e.g., 50% overlap). In one embodiment, the threshold amount of unlabeled motion data is twice the average of the cycle lengths $L_i$ of the plurality of individual cycles $\{C_i\}_{i=0}^{N-1}$ of the labeled motion data (e.g., 20 frames).

The method 200 continues, in the online processing phase, with identifying regions within the unlabeled motion data that correspond to the main feature (block 260). Particularly, once the buffer is filled with the threshold amount of unlabeled motion data, processor 122 identifies regions within the buffered unlabeled motion data that correspond to the same or essentially similar motion as the main feature $F^{main}$ for the repeated activity, which was stored in metadata. In the exemplary case that the threshold amount of unlabeled motion data is twice the average of the cycle length, then the processor 122 should identify at least two regions corresponding to the main feature $F^{main}$.

In at least some embodiments, the processor 122 is configured to utilize a sliding window approach to detect the regions corresponding to the main feature $F^{main}$ Particularly, a sliding window having a window length equaling the feature length $W_k$ of the main feature $F^{main}$ is slid across the frames in the unlabeled motion data in the buffer from beginning to end. Each particular position of the sliding window corresponds to a candidate region and is evaluated to determine its similarity with the main feature $F^{main}$ The processor 122 selects the candidate regions that are most similar to the main feature $F^{main}$ while also being sufficiently far apart from one another, as the regions corresponding to the main feature $F^{main}$.

In at least some embodiments, the processor 122 determines a respective evaluation score $S_m$, where m is the frame index within the buffer, for each position of the sliding window in the buffer or, in other words, each candidate region in the buffer. Each evaluation score $S_m$ indicates a degree of similarity between the motion data within the sliding window at the position m within the buffer and the motion data of the main feature $F^{main}$. In at least one embodiment, the processor 122 calculates the evaluation score $S_m$ for the sliding window at each position m as the average geometric distance/difference between motion data within the sliding window at the position m within the buffer and the motion data of the main feature $F^{main}$. Thus, for a given buffer of unlabeled motion data, the processor determines a set of evaluation scores $\{S_m\}_{m=0}^{M-1}$, where M is the total number of frames in the buffer.

Next, based on the set of evaluation scores $\{S_m\}_{m=0}^{M-1}$, the processor 122 is configured to identify which positions of the sliding window or, in other words, which candidate regions within the buffer, correspond to the main feature $F^{main}$ with each unlabeled cycle of the unlabeled motion data. It should be appreciated that, in the case that the evaluation score $S_m$ is the average geometric distance/difference between motion data within the sliding window at the position m within the buffer and the motion data of the main feature $F^{main}$ then the lowest scores are the best scores indicating the highest degree of similarity. Thus, in one embodiment, the processor 122 selects those sliding window positions having the lowest evaluation score $S_m$ and which are sufficiently spaced apart from one another (e.g., at least the minimum cycle length $L_i$ from the labeled motion data) as being the regions corresponding to the main feature $F^{main}$.

In one embodiment, the processor 122 is configured to determine the sliding window positions that are the regions corresponding to the main feature $F^{main}$ according to the following process. First, the processor eliminates evaluation scores $S_m$ that are not either (i) a local minimum in the set of evaluation scores $\{S_m\}_{m=0}^{M-1}$ or (2) less that a predetermined threshold score (e.g., the maximum of the set of evaluation scores $\{S_i^{best}\}_{i=0}^{N-1}$ for the set of cycle features $\{F_i^{best}\}_{i=0}^{N-1}$). In other words, only evaluation scores $S_m$ that are less than the predetermined threshold score or a local minimum are kept for consideration. Next, the processor 122 sorts the remaining evaluation scores $S_m$ from highest to lowest (i.e., worst to best). Finally, the processor 122 checks each remaining evaluation scores $S_m$, from highest to lowest. If the start position m of the corresponding window is within a threshold distance (e.g., the minimum cycle length $L_i$) the start position of an adjacent window, then the evaluation score $S_m$ is eliminated. The processor 122 performs this check iteratively from the highest to lowest remaining evaluation score $S_m$ until the only remaining evaluation scores $S_m$ are sufficiently far apart from one another (e.g., at least the minimum cycle length $L_i$). The processor 122 identifies these remaining sliding window positions as being the regions corresponding to the main feature $F^{main}$.

The method 200 continues, in the online processing phase, with identifying time boundaries between the plurality of individual cycles in the unlabeled motion data (block 270). Particularly, the processor 122 determines the time boundaries between each individual cycle of the repeated activity in the unlabeled motion data stored in the buffer. As noted above, in the exemplary case that the buffer includes unlabeled motion data that totals twice the average of the cycle length, the processor 122 identifies at least two regions corresponding to the main feature $F^{main}$. Accordingly, it should be appreciated that a time boundary between the at least two individual cycle will be located between the first region corresponding to the main feature $F^{main}$ and the second region corresponding to the main feature $F^{main}$.

The region starting from a region corresponding to the main feature $F^{main}$ and the next region corresponding to the main feature $F^{main}$ in the unlabeled motion data is denoted as a miss-aligned cycle $d_i$. The processor 122 maps the miss-aligned cycle $d_i$ to one of the re-aligned cycles $D_1$ in the set of re-aligned cycles $\{D_i\}_{i=0}^{N-2}$ using a mapping algorithm, such as a dynamic time warping algorithm. Since the time boundaries of the cycles $C_i$ have known time boundaries within the re-aligned cycles $D_i$, the processor 122 projects this known time boundary back into to the miss-aligned cycle $d_i$ of the unlabeled motion data to determine the estimated time boundary between cycles of the unlabeled motion data.

The processor 122 performs the processes of blocks 260 and 270 iteratively for each new buffer of unlabeled motion data. In this way, the processor 122 determines a plurality of time boundaries between a plurality of cycles in the unlabeled motion data, thus labeling the unlabeled motion data. From the plurality of time boundaries, the processor determines a plurality of cycle durations by calculating the time difference between consecutive time boundaries.

The method 200 continues, in the online processing phase, with outputting labels indicating the time boundaries or cycle durations for the unlabeled motion data (block 280). Particularly, the processor 122 outputs, with an output device, the time boundaries between each cycle in the plurality of cycles of the unlabeled motion data. For example, in some embodiments, the processor 122 writes the previously determined plurality of time boundaries and/or plurality of time boundaries to the memory 124. In some embodiments, the processor 122 operates the display 128 to display the previously determined plurality of time boundaries and/or plurality of time boundaries. In some embodiments, the processor operates the communication module 126 to transmit the previously determined plurality of time boundaries and/or plurality of time boundaries to another device.

Embodiments within the scope of the disclosure may also include non-transitory computer-readable storage media or machine-readable medium for carrying or having computer-executable instructions (also referred to as program instructions) or data structures stored thereon. Such non-transitory computer-readable storage media or machine-readable medium may be any available media that can be accessed by a general purpose or special purpose computer. By way of example, and not limitation, such non-transitory computer-readable storage media or machine-readable medium can comprise RAM, ROM, EEPROM, CD-ROM or other optical disk storage, magnetic disk storage or other magnetic storage devices, or any other medium which can be used to carry or store desired program code means in the form of computer-executable instructions or data structures. Combinations of the above should also be included within the scope of the non-transitory computer-readable storage media or machine-readable medium.

Computer-executable instructions include, for example, instructions and data which cause a general-purpose computer, special purpose computer, or special purpose processing device to perform a certain function or group of functions. Computer-executable instructions also include program modules that are executed by computers in stand-alone or network environments. Generally, program modules include routines, programs, objects, components, and data structures, etc. that perform particular tasks or implement particular abstract data types. Computer-executable instructions, associated data structures, and program modules represent examples of the program code means for executing steps of the methods disclosed herein. The particular sequence of such executable instructions or associated data structures represents examples of corresponding acts for implementing the functions described in such steps.

While the disclosure has been illustrated and described in detail in the drawings and foregoing description, the same should be considered as illustrative and not restrictive in character. It is understood that only the preferred embodiments have been presented and that all changes, modifications and further applications that come within the spirit of the disclosure are desired to be protected.

What is claimed is:

1. A method for recognizing repetitions of a repeated activity, the method comprising:
   receiving, with a processor, first motion data corresponding to a first plurality of repetitions of the repeated activity, the first motion data including labels identifying first time boundaries between each repetition in the first plurality of repetitions;
   identifying, with the processor, a salient segment of the first motion data corresponding to a motion of the repeated activity that occurs in all of the first plurality of repetitions;
   receiving, with the processor, second motion data corresponding to a second plurality of repetitions of the repeated activity from a motion sensing system; and
   identifying, with the processor, second time boundaries between each repetition in the second plurality of repetitions by (i) detecting at least two segments of the second motion data that are most similar to the salient segment of the first motion data, and (ii) determining at least one of the second time boundaries located between the at least two segments of the second motion data,
   wherein the detecting the at least two segments includes identifying a plurality of window segments of the second motion data, each window segment in the plurality of candidate segments including a continuous portion of motion data starting from a different time within the second motion data and having a length equal to that of the salient segment of the first motion data.

2. The method according to claim 1, the identifying the salient segment of the first motion data further comprising:
   identifying, with the processor, a plurality of candidate segments of the first motion data, each candidate segment in the plurality of candidate segments including a continuous portion of motion data starting from a different time within the first motion data;
   determining, with the processor, a respective score for each respective candidate segment in the plurality of candidate segments, the respective score indicating a level of similarity between the respective candidate segment and corresponding segments of each other repetition in the first plurality of repetitions; and
   selecting, with the processor, as the salient segment of the first motion data, the respective candidate segment of the plurality of candidate segments having the respective score that indicates a highest level of similarity of all of the plurality of candidate segments.

3. The method according to claim 2, the identifying the plurality of candidate segments further comprising:
   identifying, with the processor, for each respective repetition in the first plurality of repetitions, a respective plurality of candidate segments in the respective repetition.

4. The method according to claim 3 further comprising:
   dividing, with the processor, for each respective repetition in the first plurality of repetitions, the respective repetition into a respective plurality of frames, each frame including to a continuous portion of motion data captured during a respective interval of time.

5. The method according to claim 4, wherein, for each respective repetition in the first plurality of repetitions, each candidate segment of the respective plurality of candidate segments includes a continuous portion of motion data corresponding to a predetermined number of consecutive frames in the respective plurality of frames.

6. The method according to claim 3, the determining the respective score for each respective candidate segment further comprising:
   determining, with the processor, for each respective repetition in the first plurality of repetitions, a respective score for each respective candidate segment in the respective plurality of candidate segments in the respective repetition, the respective score indicating a level of similarity between the respective candidate segment and corresponding segments of each other repetition in the first plurality of repetitions.

7. The method according to claim 6, the determining the respective score for each respective candidate segment further comprising:
   determining, with the processor, for each respective candidate segment in the respective plurality of candidate segments in each respective repetition in the first plurality of repetitions, the corresponding segments of each other repetition in the first plurality of repetitions using a dynamic time warping algorithm.

8. The method according to claim 6, the selecting the salient segment of the first motion data further comprising:
   selecting, with the processor, for each respective repetition in the first plurality of repetitions, a respective salient segment of the respective repetition, the respective salient segment having the respective score that indicates a highest level of similarity of all of the respective plurality of candidate segments in the respective repetition.

9. The method according to claim 8, the selecting the salient segment of the first motion data further comprising:
   selecting, with the processor, as the salient segment of the first motion data, the respective salient segment having the respective score that indicates a highest level of similarity of all of the first plurality of repetitions.

10. The method according to claim 1, the receiving the second motion data further comprising:
    receiving, with the processor, the second motion data as a stream of measured motion data from the motion sensing system; and
    storing the stream of measured motion data of the second motion data in a buffer implemented on the memory.

11. The method according to claim 10, the identifying the second time boundaries further comprising:
    repeatedly performing, as further motion data of the second motion data is stored in the buffer, the (i) detecting the at least two segments of the second motion data in the buffer and (ii) the determining the at least one of the second time boundaries between the at least two segments of the second motion data in the buffer.

12. The method according to claim 1, the detecting the at least two segments further comprising:
    determining, with the processor, for each respective window segment in the plurality of window segments, a respective score indicating a level of similarity between the respective window segment and the salient segment of the first motion data.

13. The method according to claim 12, the detecting the at least two segments further comprising:
    determining, as the at least two segments of the second motion data, at least two window segments in the plurality of window segments having the respective scores that indicate a highest level of similarity with the salient segment of the first motion data, while also having in each case at least a threshold amount of time between one another.

14. The method according to claim 1, the determining the at least one of the second time boundaries further comprising:
    mapping, with the processor, a continuous portion of the second motion data that extends between two of the at least two segments of the second motion data onto the first motion data using a dynamic time warping algorithm; and
    determining, with the processor, the at least one of the second time boundaries located between the two of the at least two segments of the second motion data, based on the mapping and the labels of the first motion data.

15. The method according to claim 1, further comprising:
    storing, in a memory, metadata of the first motion data, the metadata including the salient segment of the first motion data.

16. The method according to claim 1, further comprising at least one of:
    outputting, with an output device, the second time boundaries between each repetition in the second plurality of repetitions.

17. A method for determining metadata of a repeated activity, the method comprising:
    receiving, with a processor, first motion data corresponding to a first plurality of repetitions of the repeated activity, the first motion data including labels identifying time boundaries between each repetition in the first plurality of repetitions;
    identifying, with the processor, a salient segment of the first motion data corresponding to a motion of the repeated activity that occurs in all of the first plurality of repetition by (i) identifying a plurality of candidate segments of the first motion data, each candidate segment in the plurality of candidate segments including a continuous portion of motion data starting from a different time within the first motion data, (ii) determining a respective score for each respective candidate segment in the plurality of candidate segments, the respective score indicating a level of similarity between the respective candidate segment and corresponding segments of each other repetition in the first plurality of repetitions, and (iii) selecting, with the processor, as the salient segment of the first motion data, the respective candidate segment of the plurality of candidate segments having the respective score that indicates a highest level of similarity of all of the plurality of candidate segments; and storing, in a memory, metadata of the first motion data, the metadata including the salient segment of the first motion data.

18. A method for recognizing repetitions of a repeated activity, the method comprising:
storing, in a memory, metadata of first motion data corresponding to a first plurality of repetitions of the repeated activity, the metadata including a salient segment of the first motion data corresponding to a motion of the repeated activity that occurs in all of the first plurality of repetitions;
receiving, with the processor, second motion data corresponding to a second plurality of repetitions of the repeated activity from a motion sensing system;
identifying, with the processor, time boundaries between each repetition in the second plurality of repetitions by by (i) detecting at least two segments of the second motion data that are most similar to the salient segment of the first motion data, and (ii) determining at least one of the time boundaries located between the at least two segments of the second motion data; and
outputting, with an output device, the time boundaries between each repetition in the second plurality of repetitions,
wherein the determining the at least one of the time boundaries includes (i) mapping a continuous portion of the second motion data that extends between two of the at least two segments of the second motion data onto the first motion data using a dynamic time warping algorithm and (ii) determining the at least one of the time boundaries located between the two of the at least two segments of the second motion data, based on the mapping and the labels of the first motion data.

* * * * *

UNITED STATES PATENT AND TRADEMARK OFFICE
CERTIFICATE OF CORRECTION

| | |
|---|---|
| PATENT NO. | : 11,733,259 B2 |
| APPLICATION NO. | : 17/148633 |
| DATED | : August 22, 2023 |
| INVENTOR(S) | : Lincan Zou et al. |

It is certified that error appears in the above-identified patent and that said Letters Patent is hereby corrected as shown below:

On the Title Page

In Item (72), Inventors, "Linean Zou" should read --Lincan Zou--.

Signed and Sealed this
Twenty-first Day of November, 2023

*Katherine Kelly Vidal*

Katherine Kelly Vidal
*Director of the United States Patent and Trademark Office*